(12) United States Patent
Belacel et al.

(10) Patent No.: US 7,759,060 B2
(45) Date of Patent: Jul. 20, 2010

(54) MOLECULAR METHOD FOR DIAGNOSIS OF PROSTATE CANCER

(75) Inventors: Nabil Belacel, Moncton (CA); Miroslava Cuperlovic-Culf, Moncton (CA); Rodney Ouellette, Dieppe (CA)

(73) Assignee: National Research Council of Canada, Ottawa (CA)

( * ) Notice: Subject to any disclaimer, the term of this patent is extended or adjusted under 35 U.S.C. 154(b) by 0 days.

(21) Appl. No.: 11/519,892

(22) Filed: Sep. 13, 2006

(65) Prior Publication Data

US 2007/0065856 A1    Mar. 22, 2007

(51) Int. Cl.
*C12Q 1/68*    (2006.01)
(52) U.S. Cl. .......................................................... 435/6
(58) Field of Classification Search ........................ None
See application file for complete search history.

(56) References Cited

U.S. PATENT DOCUMENTS

| | | | |
|---|---|---|---|
| 2003/0152980 A1 | 8/2003 | Golub et al. | |
| 2004/0029151 A1 | 2/2004 | Mahadevappa et al. | |

FOREIGN PATENT DOCUMENTS

| | | |
|---|---|---|
| CA | 2548528 | 6/2006 |
| WO | WO 03/012067 A2 | 2/2003 |
| WO | WO 03/016484 | 2/2003 |
| WO | WO 2004/033727 | 4/2004 |
| WO | WO 2004/091479 A2 | 10/2004 |

OTHER PUBLICATIONS

Singh et al (Cancer Cell, Mar. 2002, 1: 203-209).*
Bjefman et al (Journal of Clinical Endocrinology and Metabolism, Jul. 1997, 82(7): 2210-2214).*
Alberts et al. (Molecular Biology of the Cell, 3rd edition, 1994, p. 465).*
Greenbaum et al. (Genome Biology, 2003, vol. 4, Issue 9, pp. 117.1-117.8).*
Singh et al (Cancer Cell, Mar. 2002, 1: 203-209).*
Magee et al (Cancer Research, 2001, 5692-5696).*
Ernst T. et al., Decrease and Gain of Gene Expression Are Equally Discriminatory Markers for Prostate Carcinoma, American Journal of Pathology, Jun. 2002, 160(6): 2169-2180.
Singh D. et al., Gene Expression Correlates of Clinical Prostate Cancer Behaviour, Cancer Cell, Mar. 2002, 1: 203-209.
Landers K. A. et al., Use of Multiple Biomarkers for a Molecular Diagnosis of Prostate Cancer, Int. J. Cancer, May 10, 2005, 114: 950-956.
Mattie M. D. et al., Optimized high-throughput microRNA expression profiling provides novel biomarker assessment of clinical prostate and breat cancer biopsies, Molecular.
Cancer, Jun. 19, 2006, 5(24): 1-14.
Febbo et al, "Use of Expression Analysis to Predict Outcome After Radical Prostactemy", Journal of Urology, vol. 170,No. 6, pp. s11-s20, Dec.1, 2003.
Karaburun et al, "Relationship . . . Apoptosis Regulator Proteins (bc1-2 and p53) and Gleason Score in Prostate Cancer", Pathology Oncology Research vol. 7,No. 3, pp. 209-212, 2001.

* cited by examiner

*Primary Examiner*—Sean E Aeder
(74) *Attorney, Agent, or Firm*—Brion Raffoul (57) ABSTRACT

Methods for diagnosing or detecting cancerous prostate tissue. A panel of 8 specific marker genes are provided. The overexpression of some of these marker genes compared to their expression in normal prostate tissue and the underexpression of the rest of these marker genes are indicative of cancerous prostate tissue. By using these 8 marker genes as a diagnostic tool, smaller tissue samples, such as those obtained by core needle biopsies can be used.

4 Claims, 9 Drawing Sheets

MOLECULAR METHOD FOR DIAGNOSIS OF PROSTATE CANCER

FIELD OF THE INVENTION

The present invention relates to diagnosis methods and, more particularly, to diagnosis methods for detecting prostate cancer.

BACKGROUND TO THE INVENTION

Prostate cancer is a leading cancer in men with 20,100 new cases expected in Canada in 2004 (Canadian Cancer Statistics, 2004). An even larger number of patients, following a positive PSA (prostate specific antigen) reading undergo an invasive biopsy but are not diagnosed with cancer. Unfortunately, invasive biopsy procedures require a long hospitalization with many possible side-effects. The reason for using the more invasive biopsy procedure, as opposed to the less invasive core needle biopsy is that the standard diagnostic procedure on core needle biopsy samples has not been proven to be as accurate as a more invasive biopsy and was thereby discarded as a diagnostic modality in several countries. Although the more invasive biopsies may provide a more accurate diagnosis, they are extremely traumatic for the patient. Moreover, such procedures can potentially result in long term disabilities and constitutes a significant cost to the health system.

Current diagnostic techniques for detecting prostate cancer is based on the PSA level in the serum. The final diagnosis is determined by a pathologist checking for cancer cells in the biopsy samples.

However, these present techniques are not perfect. The PSA level in the serum can be affected by factors other then cancer, including other pathologies and age. In addition, specific properties of PSA protein in serum make accurate concentration measurements very difficult. As a result, the PSA test has a large percentage of false positive as well as false negative readings. Therefore, biopsy samples are essential for more accurate diagnosis. Unfortunately, as noted above, the preferred method of biopsy, the core needle biopsy, is often inaccurate due to the very small sample size. However, genetic testing in core needle biopsy samples will allow for the accurate diagnosis without the need for more invasive methods.

There is therefore a need for a more accurate diagnostic method that does not require an invasive biopsy to detect or diagnose prostate cancer. Ideally, such a method should be usable even with very small sample sizes and may be combined with other, pathologist-based diagnosis methods.

SUMMARY OF THE INVENTION

The present invention provides methods for diagnosing or detecting cancerous prostate tissue. A panel of 8 specific marker genes are provided. The overexpression of some of these marker genes compared to their expression in normal prostate tissue and the underexpression of the rest of these marker genes are indicative of cancerous prostate tissue. By using these 8 marker genes as a diagnostic tool, smaller tissue samples, such as those obtained by core needle biopsies can be used.

In a first aspect, the present invention provides a method for determining if prostate cells are cancerous, the method comprising:

a) obtaining said prostate cells;

b) determining if at least one specific gene is overexpressed or underexpressed in said prostate cells compared to an expression of said at least one specific gene in normal prostate cells;

c) determining that said prostate cells are cancerous based on whether said at least one gene is overexpressed or underexpressed in said prostate cells.

In another aspect, the present invention provides a use of at least one marker gene for identifying cancerous prostate tissue, an overexpression or underexpression of said at least one marker gene in prostate tissue compared to an expression of said at least one marker gene in normal prostate tissue being indicative of cancerous prostate tissue.

Yet another aspect of the invention provides a method of diagnosing prostate cancer, the method comprising:

a) obtaining prostate tissue to be diagnosed;

b) determining if specific marker genes are overexpressed or underexpressed in said prostate tissue to be diagnosed compared to non-cancerous prostate tissue;

c) determining if said prostate tissue to be diagnosed is cancerous based on an underexpression or overexpression of said specific marker genes.

BRIEF DESCRIPTION OF THE DRAWINGS

A better understanding of the invention will be obtained by considering the detailed description below, with reference to the following drawings in which.

DETAILED DESCRIPTION

The present invention relates to the use of a panel of 8 specific marker genes to diagnose or detect cancerous prostate tissue. The panel of 8 marker genes are listed in Table 1 below. Experiments have shown that this panel of marker genes give high accuracy in prostate cancer diagnosis due to the expression levels of the marker genes in cancer tissue relative to their expression levels in normal tissue.

The panel of 8 marker genes is given in Table 1. The marker genes were determined using a method developed by the inventors from the prostate tissues (normal and cancer) gene expression dataset obtained and described by Singh, D. et al. (Singh, D. et al. Gene expression correlates of clinical prostate cancer behaviour. *Cancer Cell* 1:203 (2002)).

TABLE 1

Panel of eight genes found to give high accuracy in prostate cancer diagnosis and their expression level in cancer relative to normal tissue.

| GeneBank Accession Number | Gene Name | Symbol | UniGene ID | Over or Underexpressed in cancer tissue relative to normal tissue |
|---|---|---|---|---|
| M96233 | Glutathione S-transferase M4 | GSTM4 | Hs.348387 | Underexpressed |
| Y13622 | Latent transforming growth factor beta binding protein 4 | LTBP4 | Hs.85087 | Underexpressed |
| M84526 | D component of complement (adipsin) | DF | Hs.155597 | Underexpressed |
| D83018 | Nel-like 2 | NELL2 | Hs.79389 | Underexpressed |
| Z93930 | X-box binding protein 1 | XBP1 | Hs.149923 | Overexpressed |
| AF064243 | Intersectin 1 (SH3 domain protein) | ITSN1 | Hs.66392 | Underexpressed |
| M99487 | Folate hydrolase (Prostate specific membrane antigen) 1 | FOLH1 | Hs.1915 | Overexpressed |
| X07732 | Hepsin (transmembrane protease, serine 1) | HPN | Hs.823 | Overexpressed |

Figure 1:
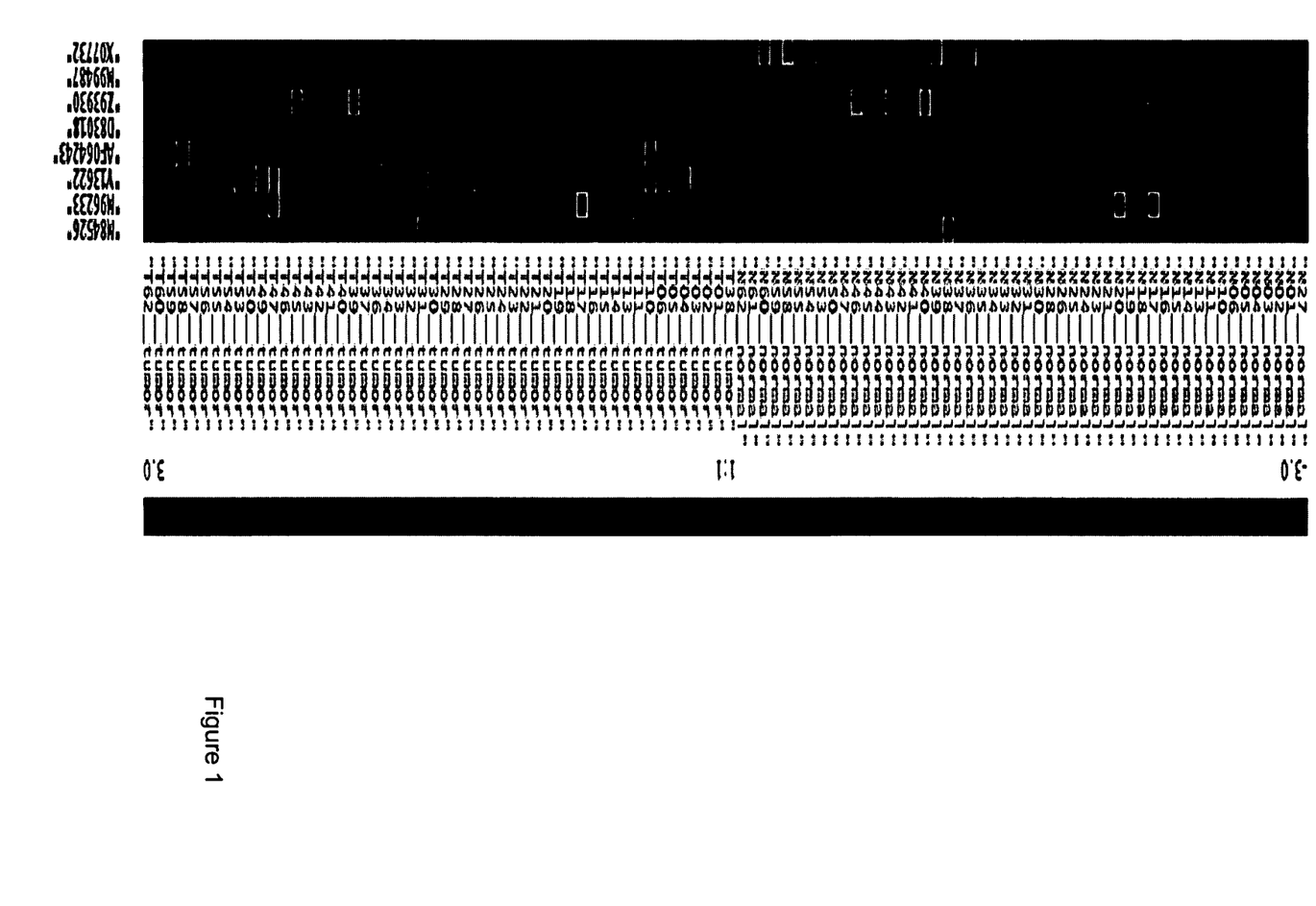
FIG. 1 is an expression plot for the 8 genes which is the subject of the present invention.

The genes listed above were derived using a microarray gene expression experiment, the gene expression plot being provided as FIG. 1 for the 8 genes. For this expression plot, the samples are normal and tumour tissues.

FIGS. 2-9 are boxplots of the comparative expression of the specific marker genes in normal prostate tissue, cancerous tissue, and other types of prostate tissue. The testing was done using the prostate microarray data available at the Oncomine database (see Rhodes D R, Yu J, Shanker K, Deshpande N, Varambally R, Ghosh D, Barrette T, Pandey A, and Chinnaiyan A M. ONCOMINE: A Cancer Microarray Database and Data-Mining Platform. Neoplasia 2004); and Rhodes D R, Yu J, Shanker K, Deshpande N., Varambally R, Ghosh D, Barrette T, Pandey A, and Chinnaiyan A M, Large-Scale Meta-Analysis of Cancer Microarray Data Identifies Common Transcriptional Profiles of Neoplastic Transformation and Progression, PNAS (2004)).

The dataset used for the experiments which resulted in the expression levels shown in the boxplots of FIGS. 2-9 included gene expressions measured using Affymetrix technology on 52 prostate tumors and 50 non-tumor prostate samples. The pre-processing included threshold readjustment (floor 50, ceiling 16,000), filtering (max/min less than 5; max-min less than 50); logarithmic transformation and standardization (to mean of zero and variance of 1). The pre-processing resulted in the set comprising 6034 genes and 102 experiments. The microarray experiments were performed on prostate tumour samples and adjacent prostate tissue not containing tumour cells (selected by a pathologist based on cell morphology, referred to as "normal") collected from patients undergoing radical prostatectomy at the Brigham and Women's Hospital, Boston, Mass. Each of these samples was reviewed by pathologist determining their Gleason Score (GS) as well as serum PSA. As noted above, microarray experiments were performed using GeneChip arrays (Affymetrix Inc.). Total RNA extracted from each sample was labeled with the fluorescence dye and hybridized to the slide in a one sample per slide format. Gene expression levels were obtained by measuring fluorescence intensities for each target (spot). Data pre-processing was performed using the standard protocol for GeneChip arrays (see Welsh J B., Analysis of gene expression identifies candidate markers and pharmacological targets in prostate cancer. Cancer Res. 61: 5974 (2001)) Data for each experiment was then scaled (normalized) to have overall mean of zero and standard deviation of one making data from different experiments comparable.

Figure 2:
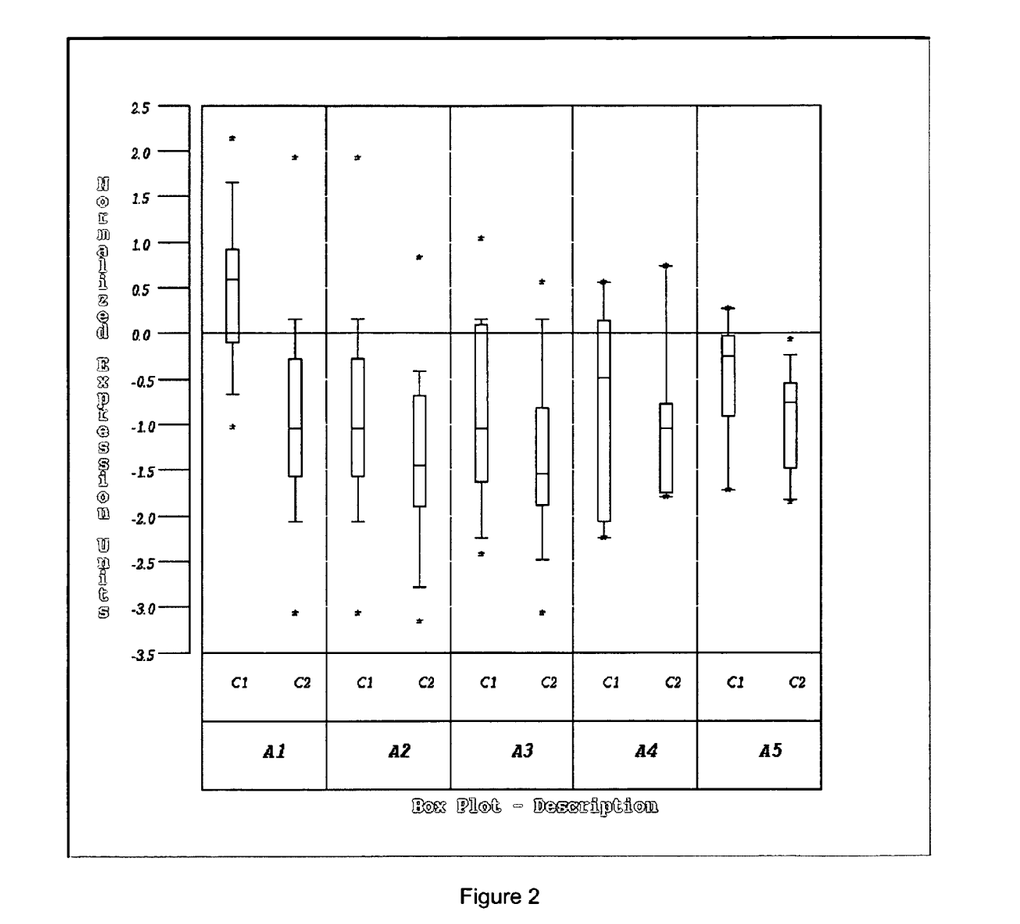
FIG. 2 is a boxplot of expression levels for the gene GSTM obtained over several experiments on prostate tissue.

Referring to FIG. 2, a boxplot of the expression levels for the gene GSTM4 obtained over several different experiments on prostate tissues is presented. Each box includes values for replicated experiments. The experiments included and the tissues used are summarized in Table 2:

TABLE 2

| Experiment | C1 | C2 | P-value |
|---|---|---|---|
| A1 [4] | BPH and Normal Prostate | Prostate Cancer | 6.366 |
| A2 [4] | Prostate Cancer | Metastatic Prostate Cancer | 0.067 |
| A3 [4] | Prostate Cancer: Gleason 6 | Prostate Cancer: Gleason 8 | 0.0823 |
| A4 [4] | Prostate Cancer: No PSA recur at 2 years | Prostate Cancer: PSA recur | 0.8647 |
| A5 [5] | Benign Prostatic Hyperplasia | Prostate Cancer | 0.1103 |

As can be seen from FIG. 2 in conjunction with Table 2 above, the gene GSTM4 is underexpressed in cancerous prostate tissue when compared to its expression in normal prostate tissue (see experiment A1 in FIG. 2). It can also be seen that, compared to the expression of this gene in normal prostate tissue, cancerous prostate tissue has a lower expression (see C1 in experiments A2-A4). Thus, for cancerous prostate tissue, the gene GSTM4 is underexpressed when compared to its expression in normal prostate tissue.

Figure 3:
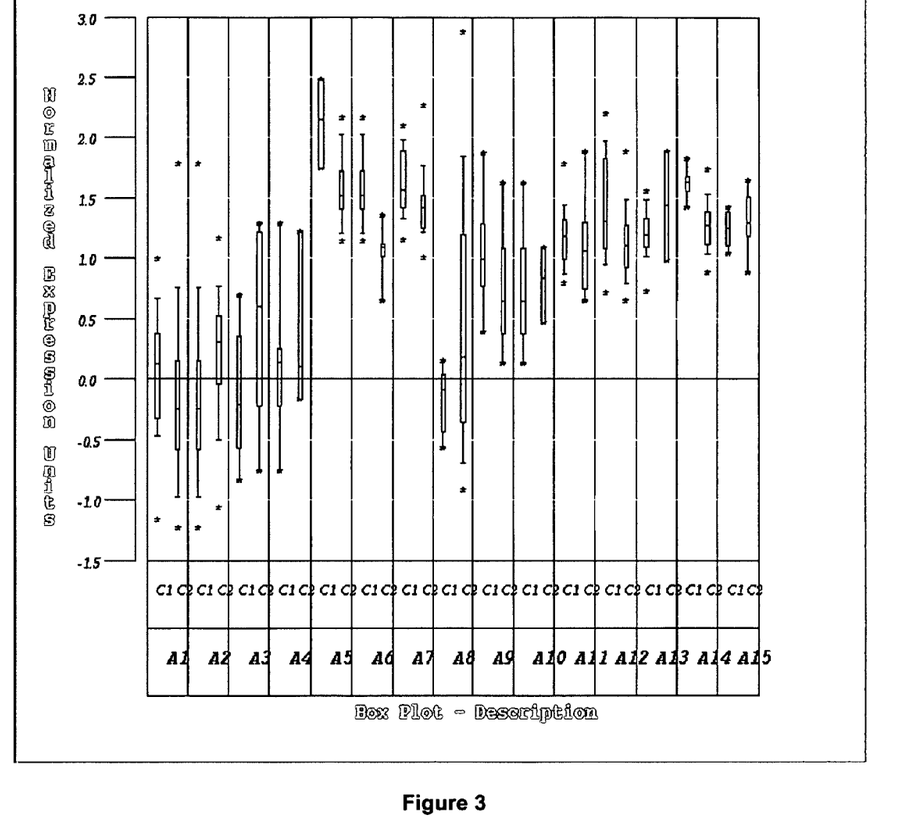
FIG. 3 is a boxplot of expression levels for the gene LTPB4 obtained over several experiments on prostate tissue.

Referring to FIG. 3, a boxplot of expression levels for the gene LTPB4 obtained over several different experiments on prostate tissues is illustrated. Each box includes values for replicated experiments. The experiments included and the tissues used are summarized in Table 3 below:

TABLE 3

| Experiment | C1 | C2 | P-value |
|---|---|---|---|
| A1 [4] | BPH and Normal Prostate | Prostate Cancer | 0.0872 |
| A2 [4] | Prostate Cancer | Metastatic Prostate Cancer | 0.0069 |
| A3 [4] | Prostate Cancer: Gleason 6 | Prostate Cancer: Gleason 8 | 0.1896 |
| A4 [4] | Prostate Cancer: No PSA recur at 2 years | Prostate Cancer: PSA recur | 0.7115 |
| A5 [6] | Normal Prostate | Prostate Cancer | 0.1142 |
| A6 [6] | Prostate Cancer | Metastatic Prostate Cancer | 1.2e-5 |
| A7 [7] | Normal Prostate | Prostate Cancer | 0.158 |
| A8 [5] | Benign Prostatic Hyperplasia | Prostate Cancer | 0.0404 |
| A9 [8] | Normal Prostate | Prostate Cancer | 1.459 |
| A10 [8] | Prostate Cancer | Metastatic Prostate Cancer | 0.7855 |
| A11 [9] | No PSA recurrence at 3 years | PSA Recurrence at 3 years | 0.6524 |
| A12 [9] | Nontumor Prostate | Prostate Cancer | 3.7e-5 |
| A13 [9] | Prostate Cancer: Gleason 6 | Prostate Cancer: Gleason 8, 9 | 0.3183 |
| A14 [10] | Normal Prostate | Prostate Cancer | 6.4e-6 |
| A15 [10] | Prostate Cancer: Gleason 6 | Prostate Cancer: Gleason 8, 9 | 0.6032 |

The results illustrated in FIG. 3 show that the gene LTPB4 is underexpressed in cancerous prostate tissue when compared to its expression in normal prostate tissue. The results of experiments A1, A5, A7, A9, A12, and A14 show that, compared to its expression in normal prostate tissue, the gene LTPB4 is underexpressed in cancerous prostate tissue. For prostate cancer tissue, the gene LTPB4 is therefore underexpressed when compared to its expression in normal prostate tissue.

Figure 4:
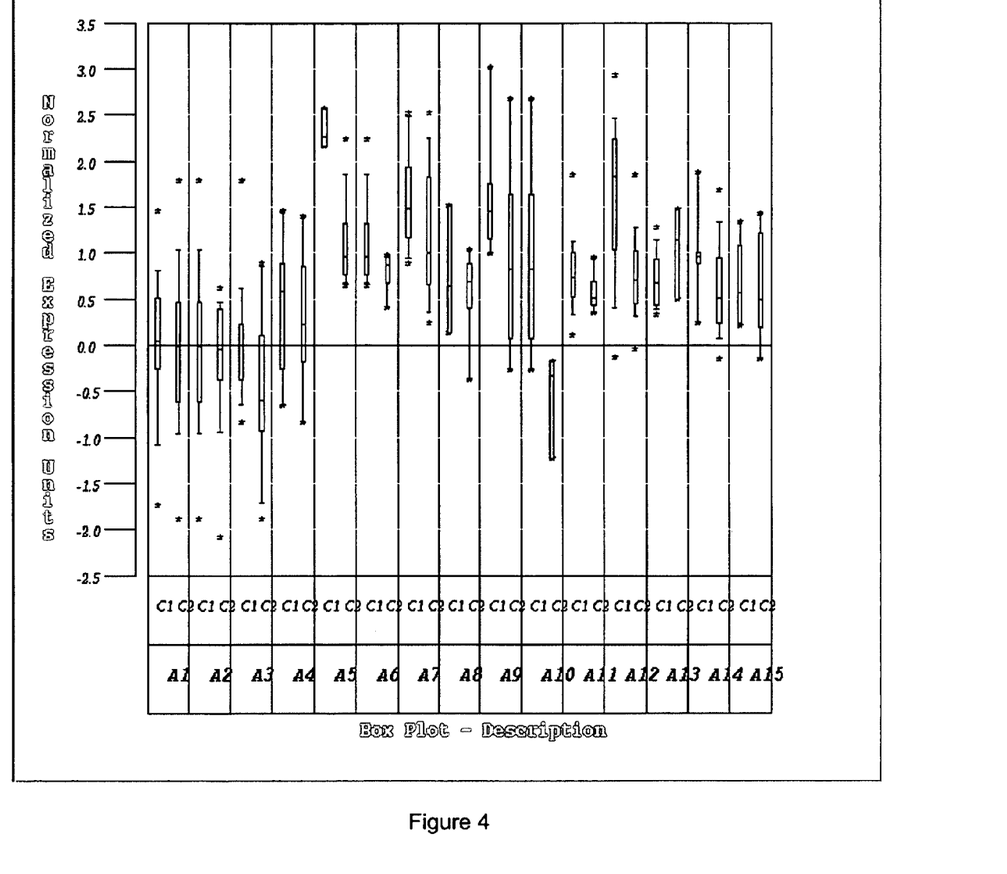
FIG. 4 is a boxplot of expression levels for the gene DF (adipsin) obtained over several experiments on prostate tissue.

Referring to FIG. 4, such is a boxplot of expression levels for the gene DF (adipsin) obtained over several different experiments on prostate tissues. Each box includes values for replicated experiments. The experiments and the prostate tissue included in the experiments are summarized in Table 4 below:

TABLE 4

| Experiment | C1 | C2 | P-value |
|---|---|---|---|
| A1 [4] | BPH and Normal Prostate | Prostate Cancer | 0.4053 |
| A2 [4] | Prostate Cancer | Metastatic Prostate Cancer | 0.7189 |
| A3 [4] | Prostate Cancer: Gleason 6 | Prostate Cancer: Gleason 8 | 0.044 |
| A4 [4] | Prostate Cancer: No PSA recur at 2 years | Prostate Cancer: PSA recur | 0.7859 |
| A5 [6] | Normal Prostate | Prostate Cancer | 0.0006 |
| A6 [6] | Prostate Cancer | Metastatic Prostate Cancer | 0.013 |
| A7 [7] | Normal Prostate | Prostate Cancer | 0.0642 |
| A8 [11] | Normal Prostate | Prostate Cancer | 0.6993 |
| A9 [8] | Normal Prostate | Prostate Cancer | 0.0893 |
| A10 [8] | Prostate Cancer | Metastatic Prostate Cancer | 0.0031 |
| A11 [9] | No PSA recurrence at 3 years | PSA Recurrence at 3 years | 0.0518 |
| A12 [9] | Nontumor Prostate | Prostate Cancer | 6.4e-10 |
| A13 [9] | Prostate Cancer: Gleason 6 | Prostate Cancer: Gleason 8, 9 | 0.2172 |
| A14 [10] | Normal Prostate | Prostate Cancer | 0.118 |
| A15 [10] | Prostate Cancer: Gleason 6 | Prostate Cancer: Gleason 8, 9 | 0.9273 |

The results in FIG. 4 show that the gene DF (adipsin) is underexpressed in cancerous prostate tissue compared to its expression in normal prostate tissue. As can be seen from the results in experiments A1, A5, A7-A9, A12, and A14, the gene DF (adipsin) has much lower expression levels in cancerous prostate tissue than in normal prostate tissue.

Figure 5:
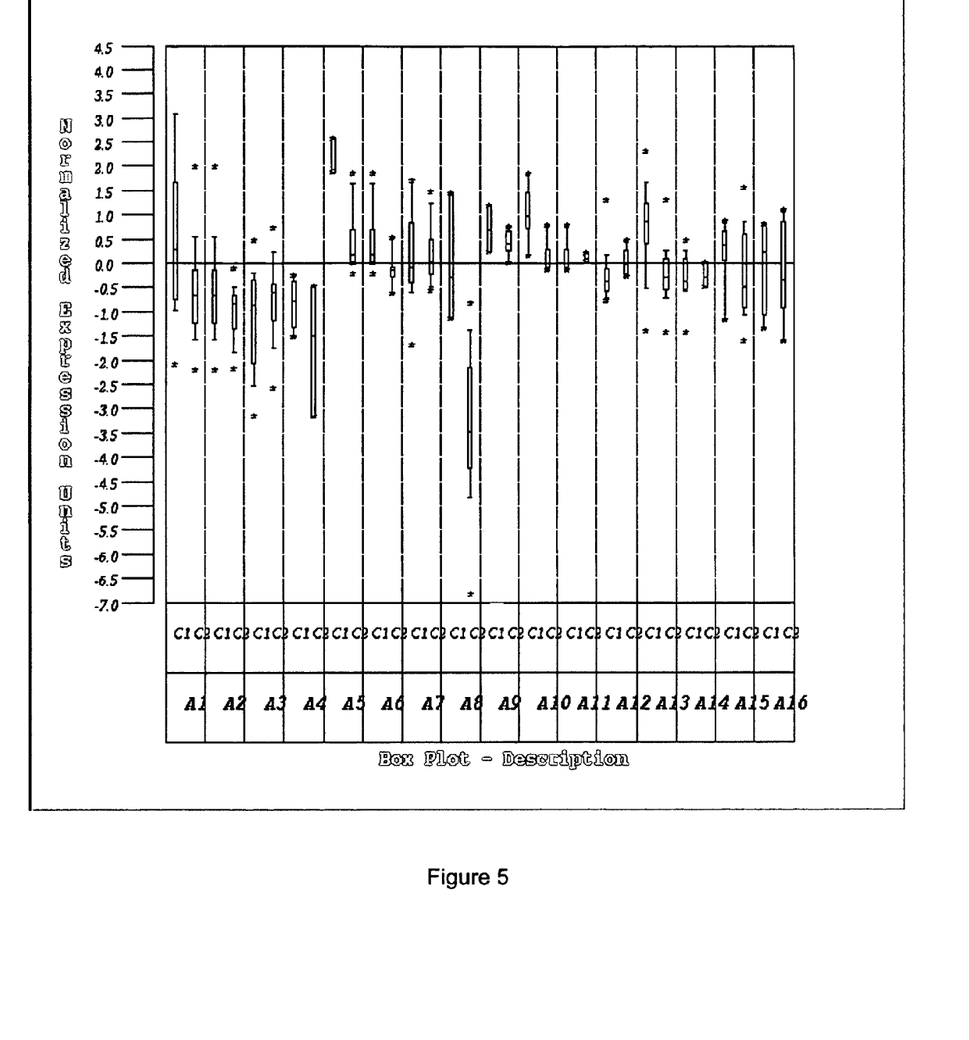
FIG. 5 is a boxplot of expression levels for the gene NELL2 obtained over several experiments on prostate tissue.

Referring to FIG. 5, a boxplot of expression levels for gene NELL2 obtained over several different experiments on prostate tissues is illustrated. Each box includes values for replicated experiments. The experiments and the types of prostate tissue used in the experiments are summarized in Table 5 below:

TABLE 5

| Experiment | C1 | C2 | P-value |
|---|---|---|---|
| A1 [4] | BPH and Normal Prostate | Prostate Cancer | 0.0039 |
| A2 [4] | Prostate Cancer | Metastatic Prostate Cancer | 0.0339 |
| A3 [4] | Prostate Cancer: Gleason 6 | Prostate Cancer: Gleason 8 | 0.3201 |
| A4 [4] | Prostate Cancer: No PSA recur at 2 years | Prostate Cancer: PSA recur | 0.3781 |
| A5 [6] | Normal Prostate | Prostate Cancer | 0.0041 |
| A6 [6] | Prostate Cancer | Metastatic Prostate Cancer | 0.0018 |
| A7 [7] | Normal Prostate | Prostate Cancer | 0.9941 |
| A8 [5] | Benign Prostatic Hyperplasia | Prostate Cancer | 4.10E-06 |
| A9 [11] | Normal Prostate | Prostate Cancer | 0.3558 |
| A10 [8] | Normal Prostate | Prostate Cancer | 0.0009 |
| A11 [8] | Prostate Cancer | Metastatic Prostate Cancer | 0.832 |
| A12 [9] | No PSA recurrence at 3 years | PSA Recurrence at 3 years | 0.0291 |
| A13 [9] | Nontumor Prostate | Prostate Cancer | 1.20E-12 |
| A14 [9] | Prostate Cancer: Gleason 6 | Prostate Cancer: Gleason 8, 9 | 0.8026 |
| A15 [10] | Normal Prostate | Prostate Cancer | 0.1714 |
| A16 [10] | Prostate Cancer: Gleason 6 | Prostate Cancer: Gleason 8, 9 | 0.6622 |

The results in FIG. 5 illustrate that the gene NELL2 underexpressed in cancerous prostate tissue when compared to its expression in non-cancerous prostate tissue. The results for the experiments A1, A5, A7, A9, A10, A13, and A14 show that the gene NELL2 has a lower expression in cancerous prostate tissue than in normal prostate tissue.

Figure 6:
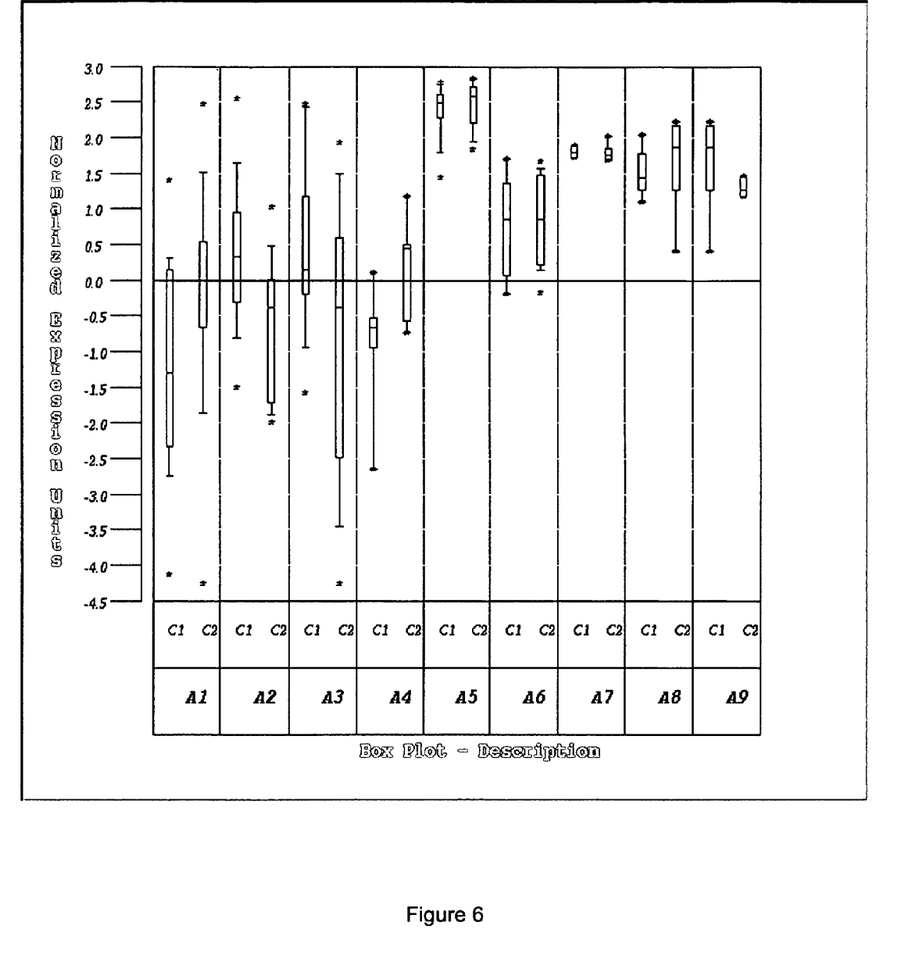
FIG. 6 is a boxplot of expression levels for the gene XBP1 obtained over several experiments on prostate tissue.

Referring to FIG. 6, a boxplot of expression levels for gene XBP1 obtained over several different experiments on prostate tissues is illustrated. Each box includes values for replicated experiments. The experiments and the types of prostate tissue used are summarized in Table 6 below:

TABLE 6

| Experiment | C1 | C2 | P-value |
|---|---|---|---|
| A1 [4] | BPH and Normal Prostate | Prostate Cancer | 0.0042 |
| A2 [4] | Prostate Cancer | Metastatic Prostate Cancer | 1.00E-04 |
| A3 [4] | Prostate Cancer: Gleason 6 | Prostate Cancer: Gleason 8 | 0.0456 |
| A4 [4] | Prostate Cancer: No PSA recur at 2 years | Prostate Cancer: PSA recur | 0.0581 |
| A5 [7] | Normal Prostate | Prostate Cancer | 0.5674 |
| A6 [5] | Benign Prostatic Hyperplasia | Prostate Cancer | 0.8723 |
| A7 [11] | Normal Prostate | Prostate Cancer | 0.8965 |
| A8 [8] | Normal Prostate | Prostate Cancer | 0.428 |
| A9 [8] | Prostate Cancer | Metastatic Prostate Cancer | 0.0697 |

FIG. 6 shows that the gene XBP1 is overexpressed in cancerous prostate tissue as opposed to normal prostate tissue. Experiments A1, A4, A5, A7 and A8 illustrate that the gene XBP1 has a lower expression level in normal prostate tissue than in cancerous prostate tissue.

Figure 7:
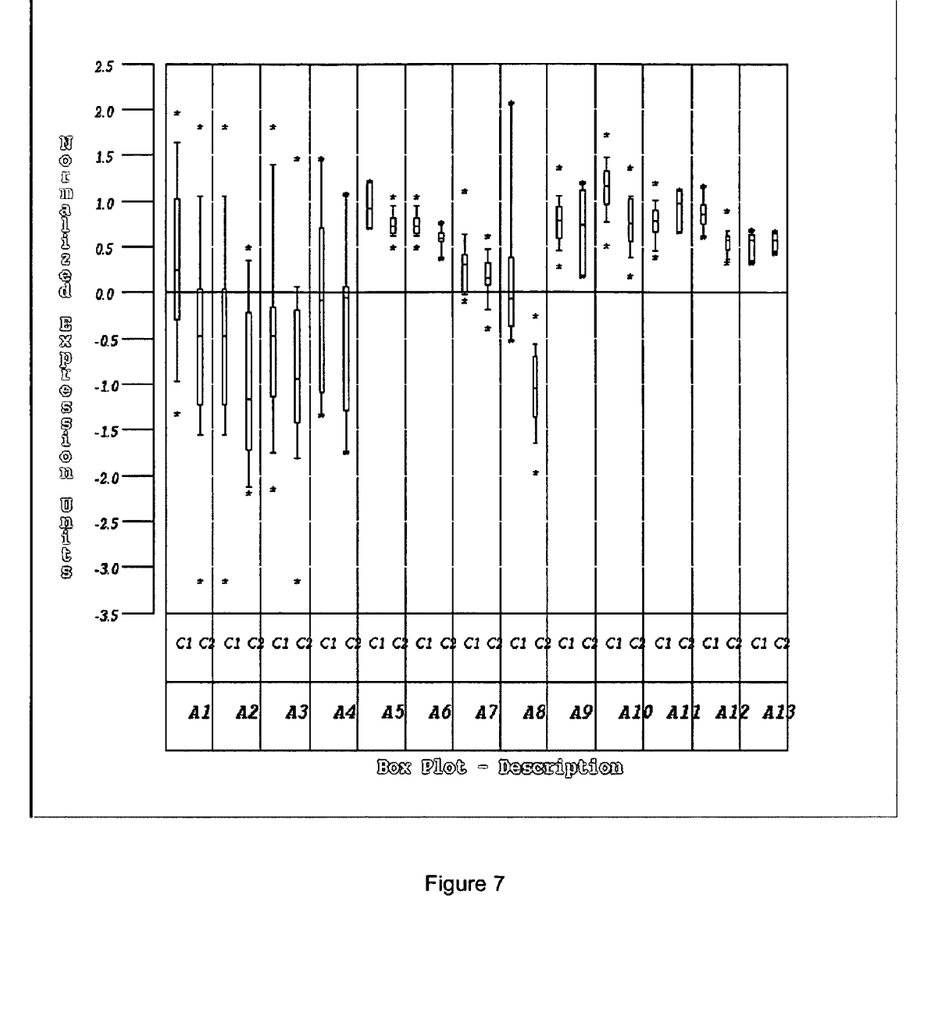
FIG. 7 is a boxplot of expression levels for the gene ITSN1 obtained over several experiments on prostate tissue.

Referring to FIG. 7, a boxplot of expression levels for gene ITSN1 obtained over several different experiments on prostate tissues is illustrated. Each box includes values for replicated experiments. The experiments and the various tissues used are summarized in Table 7 below:

TABLE 7

| Experiment | C1 | C2 | P-value |
|---|---|---|---|
| A1 [4] | BPH and Normal Prostate | Prostate Cancer | 0.0024 |
| A2 [4] | Prostate Cancer | Metastatic Prostate Cancer | 0.0106 |
| A3 [4] | Prostate Cancer: Gleason 6 | Prostate Cancer: Gleason 8 | 0.2204 |
| A4 [4] | Prostate Cancer: No PSA recur at 2 years | Prostate Cancer: PSA recur | 0.6537 |
| A5 [6] | Normal Prostate | Prostate Cancer | 0.3049 |
| A6 [6] | Prostate Cancer | Metastatic Prostate Cancer | 0.0051 |
| A7 [7] | Normal Prostate | Prostate Cancer | 0.2124 |
| A8 [5] | Benign Prostatic Hyperplasia | Prostate Cancer | 0.0021 |
| A9 [9] | No PSA recurrence at 3 years | PSA Recurrence at 3 years | 0.6691 |
| A10 [9] | Nontumor Prostate | Prostate Cancer | 3.50E−10 |
| A11 [9] | Prostate Cancer: Gleason 6 | Prostate Cancer: Gleason 8, 9 | 0.2232 |
| A12 [10] | Normal Prostate | Prostate Cancer | 0.0003 |
| A13 [10] | Prostate Cancer: Gleason 6 | Prostate Cancer: Gleason 8, 9 | 0.586 |

FIG. 7 illustrates that the gene ITSN1 has a lower expression in cancerous prostate tissue when compared to its expression in normal prostate tissue. As can be seen from the results of experiments A1, A5, A7, A10, and A12, cancerous prostate tissue has lower expression levels of ITSN1 when compared to non-cancerous prostate tissue.

Figure 8:
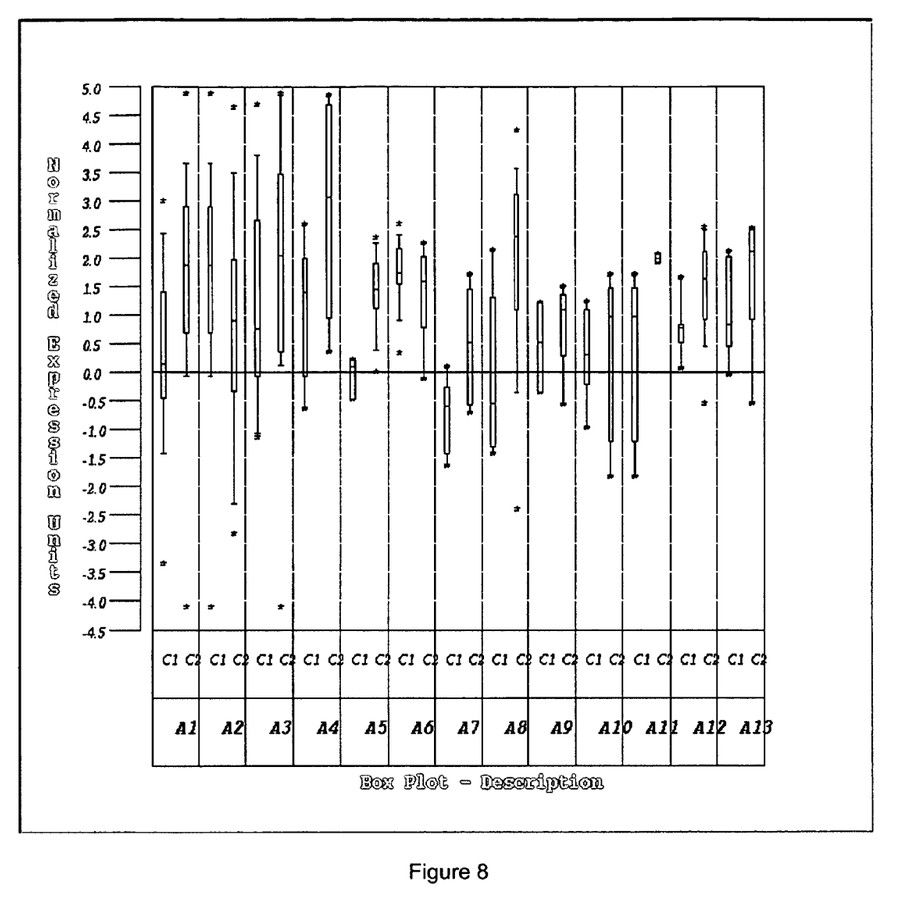
FIG. 8 is a boxplot of expression levels for the gene FOLH1 obtained over several experiments on prostate tissue.

Referring to FIG. 8, a boxplot of expression levels for gene FOLH1 obtained over several different experiments on prostate tissues is illustrated. Each box includes values for replicated experiments. The experiments and the tissues used are summarized in Table 8 below:

TABLE 8

| Experiment | C1 | C2 | P-value |
|---|---|---|---|
| A1 [4] | BPH and Normal Prostate | Prostate Cancer | 0.0011 |
| A2 [4] | Prostate Cancer | Metastatic Prostate Cancer | 0.07 |
| A3 [4] | Prostate Cancer: Gleason 6 | Prostate Cancer: Gleason 8 | 0.3748 |
| A4 [4] | Prostate Cancer: No PSA recur at 2 years | Prostate Cancer: PSA recur | 0.0801 |
| A5 [6] | Normal Prostate | Prostate Cancer | 0.0047 |
| A6 [6] | Prostate Cancer | Metastatic Prostate Cancer | 0.2598 |
| A7 [7] | Normal Prostate | Prostate Cancer | 0.0059 |
| A8 [5] | Benign Prostatic Hyperplasia | Prostate Cancer | 0.0152 |
| A9 [11] | Normal Prostate | Prostate Cancer | 0.3939 |
| A10 [8] | Normal Prostate | Prostate Cancer | 0.8983 |
| A11 [8] | Prostate Cancer | Metastatic Prostate Cancer | 0.0123 |
| A12 [10] | Normal Prostate | Prostate Cancer | 0.0039 |
| A13 [10] | Prostate Cancer: Gleason 6 | Prostate Cancer: Gleason 8, 9 | 0.2576 |

FIG. 8 illustrates that the gene FOLH1 is overexpressed in cancerous prostate tissue as compared to normal prostate tissue. The results of experiments A1, A5, A7, A9, A10, and A12 show that the gene FOLH1 has a higher expression in cancerous prostate tissue than in normal prostate tissue.

Figure 9:
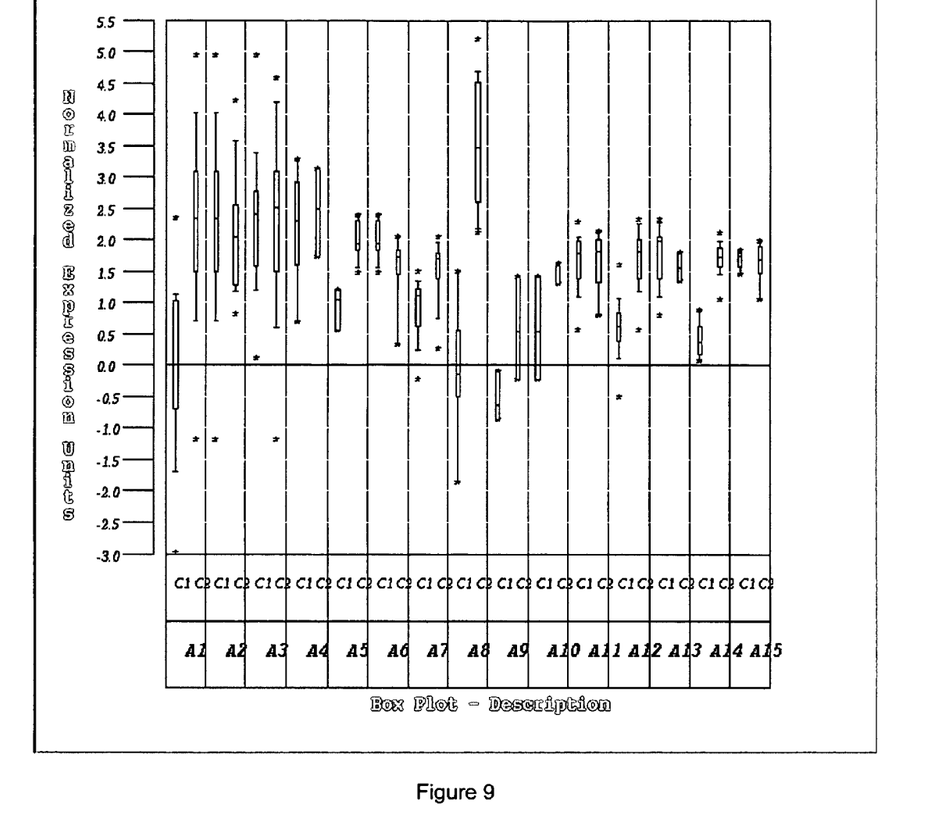
FIG. 9 is a boxplot of expression levels for the gene Hepsin obtained over several experiments on prostate tissue.

Referring to FIG. 9, a boxplot of expression levels for gene Hepsin obtained over several different experiments on prostate tissues is illustrated. Each box includes values for replicated experiments. The experiments and the different types of prostate tissue used are summarized in Table 9 below:

TABLE 9

| Experiment | C1 | C2 | P-value |
|---|---|---|---|
| A1 [4] | BPH and Normal Prostate | Prostate Cancer | 1.60E−08 |
| A2 [4] | Prostate Cancer | Metastatic Prostate Cancer | 0.3311 |
| A3 [4] | Prostate Cancer: Gleason 6 | Prostate Cancer: Gleason 8 | 0.8772 |
| A4 [4] | Prostate Cancer: No PSA recur at 2 years | Prostate Cancer: PSA recur | 0.5244 |
| A5 [6] | Normal Prostate | Prostate Cancer | 0.0205 |
| A6 [6] | Prostate Cancer | Metastatic Prostate Cancer | 0.0351 |
| A7 [7] | Normal Prostate | Prostate Cancer | 0.0017 |
| A8 [5] | Benign Prostatic Hyperplasia | Prostate Cancer | 1.80E−07 |
| A9 [8] | Normal Prostate | Prostate Cancer | 0.0484 |
| A10 [8] | Prostate Cancer | Metastatic Prostate Cancer | 0.0662 |
| A11 [9] | No PSA recurrence at 3 years | PSA Recurrence at 3 years | 0.866 |
| A12 [9] | Nontumor Prostate | Prostate Cancer | 6.10E−25 |
| A13 [9] | Prostate Cancer: Gleason 6 | Prostate Cancer: Gleason 8, 9 | 0.2081 |
| A14 [10] | Normal Prostate | Prostate Cancer | 2.10E−08 |
| A15 [10] | Prostate Cancer: Gleason 6 | Prostate Cancer: Gleason 8, 9 | 0.7475 |

From FIG. 9, it can be seen that the gene Hepsin is overexpressed in cancerous prostate tissue as opposed to normal prostate tissue. The results of experiments A1, A5, A7, A8, A9, A12, and A14 show that Hepsin has a higher expression in cancerous prostate tissue than in normal prostate tissue.

The qualitative agreement between the differences in expression in cancer and normal prostate tissues for the eight genes investigated here is good overall with most genes showing significant difference between cancer and normal tissue as well as benign and malignant tumours in the majority of experiments. The results shown here prove that a subset of 8 genes is an appropriate diagnostic panel regardless of the experimental conditions. At the same time, in some cases, especially for the gene LTPB4, there are changes in the relative expression in cancer against normal prostate tissue depending on the experiment. Such variations show that it is preferable that one looks at the overall result for the whole panel and that diagnostics based on only one gene may be unreliable.

It should be noted that expression analysis can be carried out using any method for measuring gene expression. Such methods as microarrays, diagnostic panel mini-chip, PCR, real-time PCR, and other similar methods may be used. Similarly, methods for measuring protein expression may also be used.

As noted above, the cancerous prostate cells can be obtained from a patient using needle biopsy or even from prostate cancer cells present in the blood stream. Normal or non-cancerous prostate cells against which the cancerous cells can be compared can also be obtained from the patient or from other patients. Experiments have shown that the diagnosis can be possible from just a small number of cancer cells.

While it is preferable that the complete panel of 8 marker genes be used in the diagnosis of possible prostate cancer, using a subset of the 8 marker genes will also yield useful results. Using a panel of anywhere from 1 to 7 marker genes out of the 8 marker genes on suspect prostate tissue will still provide a useful indication as to whether cancerous prostate tissue may be present or whether further and more involved tests are required.

A person understanding this invention may now conceive of alternative structures and embodiments or variations of the above all of which are intended to fall within the scope of the invention as defined in the claims that follow.

We claim:

1. A method for determining if prostate cells are cancerous, the method consisting of:
   a) obtaining said prostate cells;
   b) determining an expression of polynucleotides encoding Hepsin (transmembrane protease serine 1) genes in said prostate cells relative to normal prostate cells;
   c) determining an expression of polynucleotides encoding X-box binding protein 1 genes in said prostate cells relative to normal prostate cells;
   d) determining an expression of polynucleotides encoding Folate hydrolase (Prostate specific membrane antigen) 1 genes in said prostate cells relative to normal prostate cells;
   e) determining an expression of polynucleotides encoding Glutathione S-transferase M4 genes in said prostate cells relative to normal prostate cells;
   f) determining an expression of polynucleotides encoding Intersectin 1 (SH3 domain protein) genes in said prostate cells relative to normal prostate cells;
   g) determining an expression of polynucleotides encoding Nel-like 2 genes in said prostate cells relative to normal prostate cells;
   h) determining an expression of polynucleotides encoding D component of complement (adipsin) genes in said prostate cells relative to normal prostate cells;
   i) determining an expression of polynucleotides encoding Latent transforming growth factor beta binding protein 4 genes in said prostate cells relative to normal prostate cells;
   j) determining that said prostate cells are cancerous in the event that said polynucleotides encoding
      Hepsin (transmembrane protease serine 1);
      X-box binding protein 1; and
      Folate hydrolase (Prostate specific membrane antigen) 1;
   genes are overexpressed in said prostate cells relative to normal prostate cells and in the event that said polynucleotides encoding
      Glutathione S-transferase M4;
      Intersectin 1 (SH3 domain protein);
      Nel-like 2;
      D component of complement (adipsin); and
      Latent transforming growth factor beta binding protein 4;
   genes are underexpressed in said prostate cells relative to normal prostate cells.

2. The method according to claim 1 wherein said prostate cells are obtained by a core needle biopsy.

3. A method of diagnosing prostate cancer, the method consisting of:
   a) obtaining a prostate tissue to be diagnosed;
   b) determining an expression of polynucleotides encoding Hepsin (transmembrane protease serine 1) genes in said prostate tissue relative to normal prostate tissue;
   c) determining an expression of polynucleotides encoding X-box binding protein 1 genes in said prostate tissue relative to normal prostate tissue;
   d) determining expression of polynucleotides encoding Folate hydrolases (prostate specific membrane antigen) 1 genes in said prostate tissue relative to normal prostate tissue;
   e) determining an expression of polynucleotides encoding Glutathione S-transferase M4 genes in said prostate tissue relative to normal prostate tissue;
   f) determining an expression of polynucleotides encoding Intersectin 1 (SH3 domain protein) genes in said prostate tissue relative to normal prostate tissue;
   g) determining an expression of polynucleotides encoding Nel-like 2 genes in said prostate tissue relative to normal prostate tissue;
   h) determining an expression of polynucleotides encoding D component of complement (adipsin) genes in said prostate tissue relative to normal prostate tissue;
   i) determining an expression of polynucleotides encoding Latent transforming growth factor beta binding protein 4 genes in said prostate tissue relative to normal prostate tissue;
   j) determining that said prostate tissue is cancerous when said polynucleotides encoding
      Hepsin (transmembrane protease serine 1);
      X-box binding protein 1; and
      Folate hydrolases (Prostate specific membrane antigen) 1;
   genes are overexpressed in said prostate tissue relative to normal prostate tissue and when said polynucleotides encoding
      Glutathione S-transferase M4;
      Intersectin 1 (SH3 domain protein);
      D component of complement (adipsin); and
      latent transforming growth factor beta binding protein 4;
   genes are underexpressed in said prostate tissue relative to normal prostate tissue.

4. The method according to claim 3 wherein said prostate tissue is obtained by a core needle biopsy.

* * * * *